(12) United States Patent
Kennedy (10) Patent No.: US 11,488,292 B2
(45) Date of Patent: Nov. 1, 2022

(54) ENHANCED FLUORESCENCE IMAGING FOR IMAGING SYSTEM

(71) Applicant: KARL STORZ Imaging, Inc., Goleta, CA (US)

(72) Inventor: Bryan Kennedy, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 17/128,586

(22) Filed: Dec. 21, 2020

(65) Prior Publication Data

US 2021/0110521 A1    Apr. 15, 2021

Related U.S. Application Data

(63) Continuation of application No. 16/597,435, filed on Oct. 9, 2019, now Pat. No. 10,902,572.

(51) Int. Cl.
*G06T 5/50*      (2006.01)
*G06T 7/30*      (2017.01)
(Continued)

(52) U.S. Cl.
CPC ............... *G06T 5/50* (2013.01); *A61B 1/043* (2013.01); *A61B 1/0638* (2013.01);
(Continued)

(58) Field of Classification Search
CPC .. G06T 5/50; G06T 5/007; G06T 5/20; G06T 7/30; G06T 2207/10048;
(Continued)

(56) References Cited

U.S. PATENT DOCUMENTS 4,805,129 A    2/1989  Morgan
5,384,869 A    1/1995  Wilkinson
(Continued)

FOREIGN PATENT DOCUMENTS

WO    2019003751 A1    1/2019

OTHER PUBLICATIONS

Hemb, Björn; Extended European Search Report, dated Jan. 28, 2021 pp. 1-7; Munich, Germany Application 20196072.1-1126.
(Continued)

*Primary Examiner* — Nasim N Nirjhar
(74) *Attorney, Agent, or Firm* — Honigman LLP (57) ABSTRACT

A fluorescence imaging system is configured to generate a video image onto a display. The system includes a light source for emitting infrared light and white light, an infrared image sensor for capturing infrared image data, and a white light image sensor for capturing white light image data. Data processing hardware performs operations that include filtering the infrared image data with a first digital finite impulse response (FIR) filter configured to produce a magnitude response of zero at a horizontal Nyquist frequency and a vertical Nyquist frequency. The operations also include filtering the infrared image data with a second digital FIR filter configured with a phase response to spatially align the white light image data with the infrared image data. The operations also include combining the white light image data and the infrared image data into combined image data and transmitting the combined image data to the display.

18 Claims, 11 Drawing Sheets

(51) Int. Cl.
    *H04N 9/04*       (2006.01)
    *A61B 1/04*        (2006.01)
    *A61B 1/06*        (2006.01)
    *A61B 5/00*        (2006.01)
    *G02B 27/10*      (2006.01)
    *G02B 27/12*      (2006.01)
    *G06T 5/00*        (2006.01)
    *G06T 5/20*        (2006.01)
    *H04N 5/225*      (2006.01)
    *H04N 5/235*      (2006.01)

(52) U.S. Cl.
    CPC ........ *A61B 5/0071* (2013.01); *G02B 27/1013* (2013.01); *G02B 27/126* (2013.01); *G06T 5/007* (2013.01); *G06T 5/20* (2013.01); *G06T 7/30* (2017.01); *H04N 5/2256* (2013.01); *H04N 5/2258* (2013.01); *H04N 5/2352* (2013.01); *H04N 9/0455* (2018.08); *G06T 2207/10048* (2013.01); *G06T 2207/10064* (2013.01); *G06T 2207/10068* (2013.01); *G06T 2207/20221* (2013.01); *H04N 2005/2255* (2013.01)

(58) Field of Classification Search
    CPC . G06T 2207/10064; G06T 2207/10068; G06T 2207/20221; G06T 5/002; A61B 1/043; A61B 1/0638; A61B 5/0071; A61B 1/00163; A61B 1/00009; G02B 27/1013; H04N 5/2256; H04N 5/2258; H04N 5/2352; H04N 9/0455; H04N 2005/2255
    See application file for complete search history.

(56) References Cited

U.S. PATENT DOCUMENTS

| | | | |
|---|---|---|---|
| 2012/0071765 A1* | 3/2012 | Chinnock | A61B 5/0075 600/476 |
| 2014/0282624 A1* | 9/2014 | Holt | G06T 1/20 719/318 |
| 2015/0182118 A1* | 7/2015 | Bradbury | A61B 1/00006 600/431 |
| 2021/0168307 A1* | 6/2021 | Ma | B64C 39/024 |

OTHER PUBLICATIONS

Tsuhan Chen et al; Multidimensional Multirate Filters and Filter Banks Derived from One-Dimentional Filters, IEEE Transactions on Signal Processing, May 1993, pp. 1749-1765, vol. 4, No. 5, IEEE New York, US.

* cited by examiner

Red Chan  Blue Chan  Green Chan

ENHANCED FLUORESCENCE IMAGING FOR IMAGING SYSTEM

TECHNICAL FIELD

The disclosure relates to an enhanced fluorescence imaging system for medical procedures.

BACKGROUND

Endoscopes are commonly used to provide access to body cavities while decreasing the invasiveness of a surgical procedure. The endoscope may include one or more light sources that emit both white (i.e., visible) light and infrared light. The white light is typically used as a reference light or illuminating light, while the infrared light is typically used as an excitation light. That is, the infrared light is used to irradiate medication (e.g., dye) administered to a patient with infrared light, which in turn causes the medication to emit fluorescence light. The endoscope includes one or more image sensors to capture the reflected white light and/or the emitted fluorescence light. However, often the quantum efficiency of these image sensors is lacking, thus causing the sensitivity and contrast of the images to suffer. While image sensors with higher quantum efficiencies are available, their use in endoscopy is limited due to issues such as sensitivity, phase misalignment, and contrast loss.

SUMMARY

One aspect of the disclosure provides a system for enhanced fluorescence imaging. The system includes a light source for emitting infrared light and white light, an infrared image sensor for capturing infrared image data in the infrared spectrum, and a white light image sensor for capturing white light image data in the white light spectrum. The system also includes data processing hardware in communication with the infrared image sensor and the white light image sensor and memory hardware in communication with the data processing hardware. The memory hardware stores instructions that when executed on the data processing hardware cause the data processing hardware to perform operations that include filtering the infrared image data with fluorescence image enhancer having a first digital finite impulse response (FIR) filter and a second digital FIR filter. The first digital FIR filter is configured to produce a magnitude response of zero at a horizontal Nyquist frequency and a vertical Nyquist frequency. The second digital FIR filter is configured with a phase response to spatially align the white light image data with the infrared image data. The operations also include combining the aligned white light image data and the aligned and filtered infrared image data into combined image data and transmitting the combined image data to the display.

Implementations of the disclosure may include one or more of the following optional features. In some implementations, the fluorescence image enhancer further includes a third digital FIR filter that is configured to equalize for contrast loss from fluorescence diffusion. In some examples, the fluorescence image enhancer further includes a fourth digital FIR filter that is configured to adjust a sensitivity of the infrared image data and a contrast of the infrared image data based on received infrared light. The fourth digital FIR filter may include a low pass filter with a cutoff frequency and a magnitude. Optionally, the fourth digital FIR filter is further configured to increase the sensitivity of the infrared image data and decrease the contrast of the infrared image data when the received infrared light is below a threshold level.

In some implementations, the fourth digital FIR filter adjusts the infrared image data by increasing the sensitivity of the infrared image data and decreasing the contrast of the infrared image data when the received infrared light is below a threshold level. The fourth digital FIR filter may be further configured to increase the sensitivity of the infrared image data by increasing the magnitude and decrease the contrast of the infrared image data by decreasing the cutoff frequency when the received infrared light is below a threshold level. The fourth digital FIR filter, in some examples, adjusts the infrared data by decreasing the sensitivity of the infrared image data and increasing the contrast of the infrared image data when the ambient light level is above a threshold level. The fourth digital FIR filter may be further configured to decrease the sensitivity of the infrared image data by decreasing the magnitude and increase the contrast of the infrared image data by increasing the cutoff frequency when the received infrared light is below a threshold level.

In some implementations, the fourth digital FIR filter is configured to adjust the sensitivity and the contrast of the infrared image data by adjusting an accumulation of light in a neighborhood of the infrared image data. The infrared image sensor and the white light image sensor may have the same resolution. The infrared image sensor, in some examples, includes a near infrared image sensor. Optionally, the infrared image sensor and the white light image sensor comprise a Bayer color filter array.

In some implementations, the system further includes a dichroic prism. The dichroic prism splits received light into white light and infrared light and the infrared image sensor receives the infrared light from the dichroic prism and the white light image sensor receives the white light from the dichroic prism. The first digital FIR filter may be further configured to produce a flat magnitude response prior to the horizontal Nyquist frequency and the vertical Nyquist frequency. The second digital FIR filter may be configured to spatially adjust a position of the infrared image data in two dimensions.

The details of one or more implementations of the disclosure are set forth in the accompanying drawings and the description below. Other aspects, features, and advantages will be apparent from the description and drawings, and from the claims.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

DETAILED DESCRIPTION OF PREFERRED EMBODIMENTS

Implementations herein are directed toward an enhanced fluorescence imaging system that reconstructs a fluorescent dye image from color filter array (CFA) channels with minimal CFA modulation and maximally flat spatial frequency response (SFR). The imaging system improves sensitivity of the infrared image sensor output over previous systems, while adaptively controlling the sensitivity improvement by using an extended precision parametrically controlled two-dimensional (2D) low-pass filter. The imaging system may also correct for misregistration of the fluorescing dye and white light prism output images and correct for diffusion-based contrast loss in the image. As used herein, the term "fluorescent dye" refers to dye approved for medical use that is configured to reflect infrared light such as Indocyanine Green (ICG).

Endoscopy, a nonsurgical medical procedure used to examine internal body cavities (e.g., a digestive tract), is increasingly used as an effective diagnostic tool. The procedures are typically performed using endoscopes, which include, in their most basic form, a flexible tube with a light source and a camera. The flexible tube is passed through an orifice (e.g., the mouth) of a patient and the camera records images illuminated by the light.

In addition to visible white light, many endoscopes are capable of emitting other spectrums of light. For example, it is common for endoscopes to also emit infrared light to support fluorescent imaging. ICG is a cyanine dye used frequently in medical diagnostics and endoscopy for determining cardiac output, hepatic function, liver and gastric blood flow, and for ophthalmic angiography. For example, ICG distribution within the tissue enables intraoperative evaluation of a tissue perfusion and vacuolization, identification of critical neurovascular structures and differentiation of tissue plains between lesions and adjacent structures. ICG has a peak spectral absorption in the near infrared spectrum at approximately 800 nm. The dye, after being administered intravenously, acts as an indicator substance by binding tightly to plasma proteins within the vascular system. ICG, when irradiated with light between 750 nm and 950 nm, emits fluorescence. The endoscope, after irradiating the ICG with the near infrared light, detects and images this fluorescence.

Endoscopes may be equipped with one or more image sensors to image both white (i.e., visible) light and infrared light. For example, some endoscopes are equipped with a three charge-coupled device (3CCD) camera. A 3CCD camera uses a prism to split received light into three beams, one of which is directed to a red CCD, one to a green CCD, and one to a blue CCD. These imagers tend to have a very low quantum efficiency (see FIG. 3). That is, the ratio of incident photons converted to electrons may be very low, yielding poor sensitivity. Endoscopes, in some examples, are equipped with multiple image sensors with each sensor dedicated to a respective frequency band using a filter commonly known as a Bayer filter (see FIG. 2). In some instances, this allows the image sensors to have a significantly higher quantum efficiency (see FIG. 4).

For illustrative purposes, a description of a fluorescence image enhancer is provided within the context of an endoscopic system 100. However, it should be appreciated that the fluorescence image enhancer may be utilized in other applications, illustratively including an exoscope, borescopes and other systems having two or more illumination-types and one or more image sensors. Furthermore, although the system is described with respect to medical applications using fluorescing dye, it should be understood that industrial applications using other combinations of white light and colored light of narrow wavelength ranges may benefit from the same principles.

Figure 1:
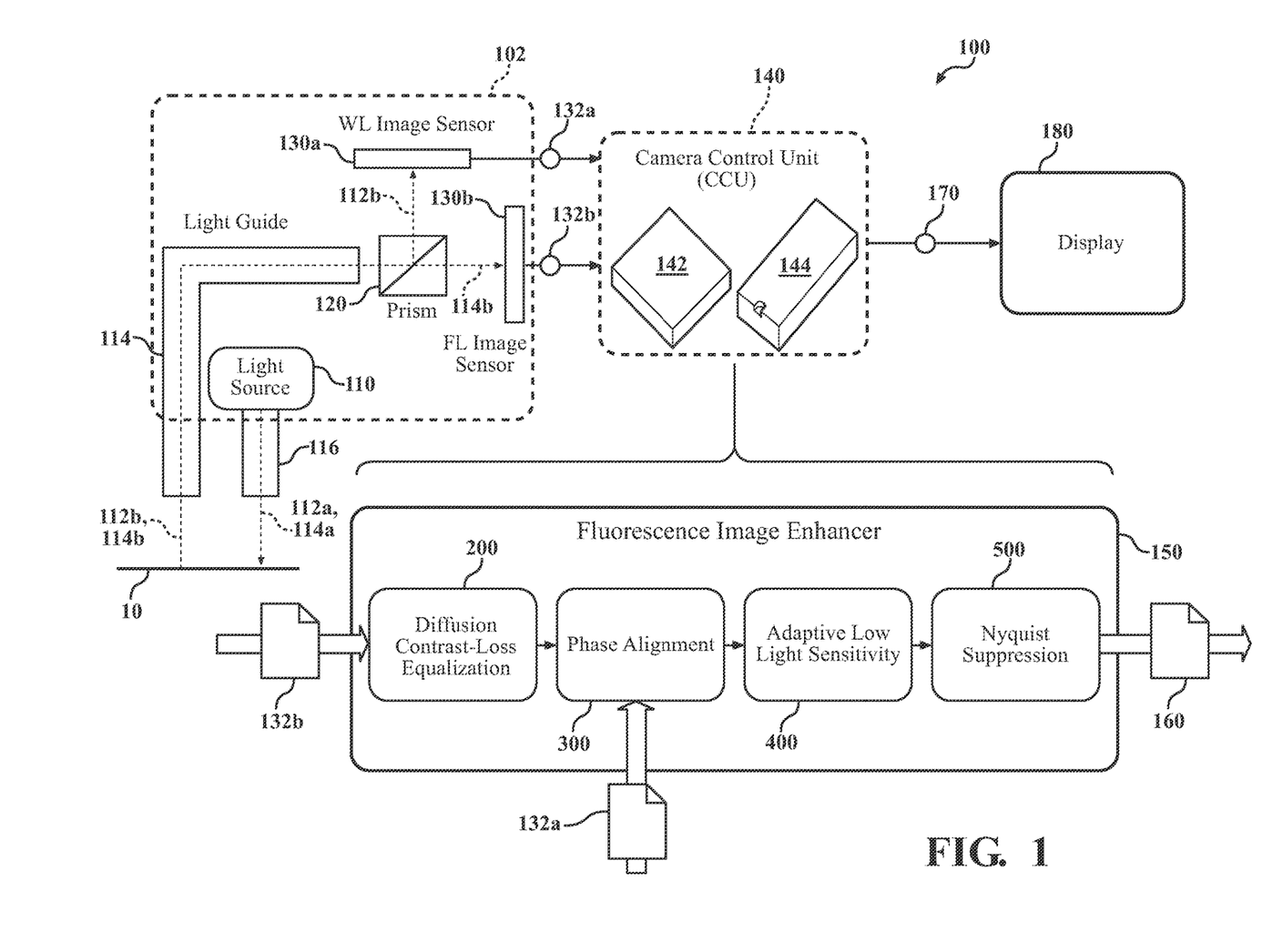
FIG. 1 is a schematic view of an example system for enhanced fluorescence imaging.

Referring to FIG. 1, in some implementations, an endoscopic example system 100 includes one or more light sources 110. The light source 110 emits both white light (WL) 112*a* and near infrared light (NIR) 114*a* (sometimes referred to as color light). While the light source(s) 110 may emit the WL 112*a* and the NIR light 114*a* simultaneously, typically the light source 110 alternates between emitting WL 112*a* and NIR light 114*a*. That is, in some examples, the light source 110 rapidly switches between emitting WL 112*a* and NIR light 114*a*. The WL 112*a* illuminates the surgical site of the system 100. The light source 110 may include one or more light-emitting diodes (LEDs) or any other appropriate light-emitting device. Separate light sources may emit the WL 112*a* and the MR light 114*a* respectively. In some examples, the light source 110 is included within a camera head unit 102.

Light 112*a*, 114*a* emitted by the light source 110 travels along a light guide 116 (e.g., an optical fiber) and, after exiting the light guide 116, illuminates or irradiates a target area 10 (e.g., an internal cavity of a patient). Reflected WL 112*b* (i.e., WL 112*a* that has reflected from the target area 10) and emitted fluorescent light (FL) 114*b* (i.e., light emitted by, for example, ICG that has been irradiated by MR light 114*a*) is directed back through the light guide 116 to a dichroic prism 120. The dichroic prism 120 splits received light into two beams of differing wavelength. That is, the dichroic prism 120 splits the received light, which may include reflected WL 112*b* and/or FL 114*b*, to image sensors 130*a*, 130*b*. For example, any reflected WL 112*b* (i.e., visible light) that passes through the prism 120 may be directed to the WL image sensor 130*a*, while any FL 114*b* that passes through the prism 120 may be directed to the FL image sensor 130*b* (i.e., light with a wavelength between 800 nm and 1200 nm). In some examples, the prism 120 and image sensors 130 are also included within the camera head unit 102.

Figure 2:
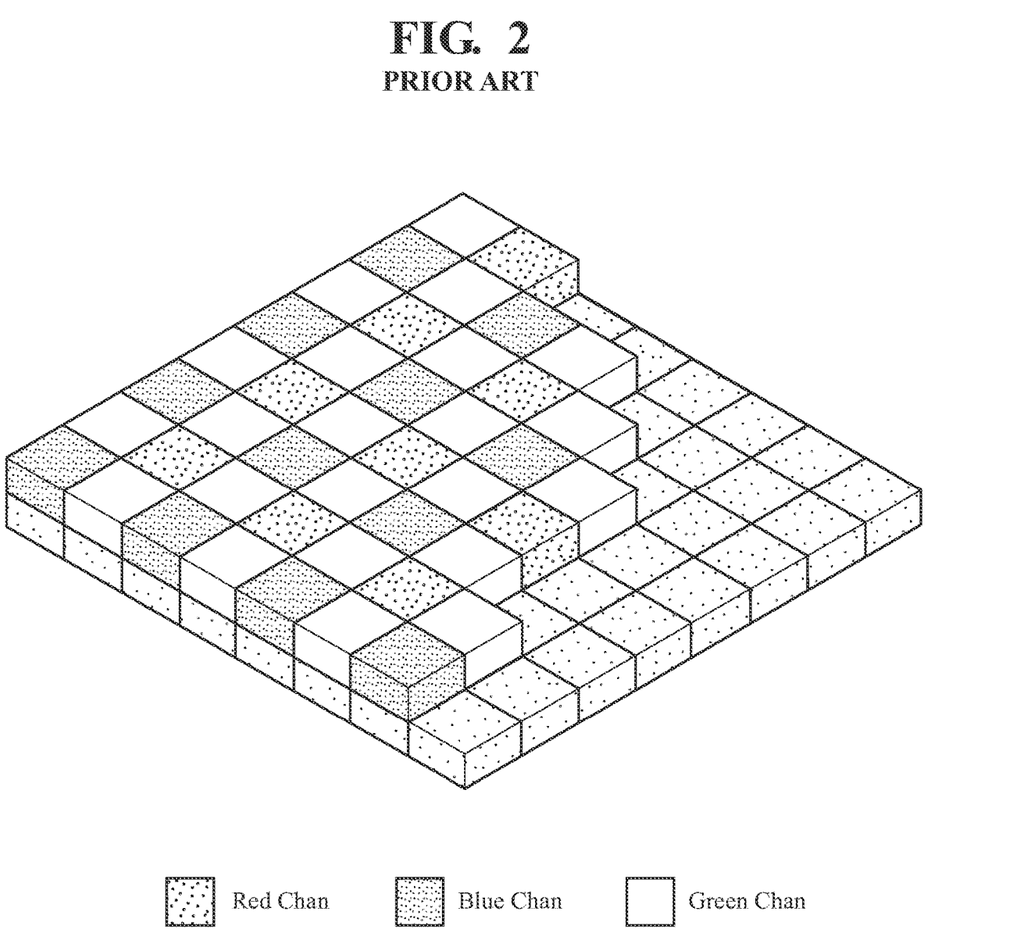
FIG. 2 is a perspective view of a known Bayer color filter array image sensor.

The image sensors 130 may be a complementary metal oxide semiconductor (CMOS) or a Charged Coupled Device (CCD). It should be appreciated that any pixelated image sensor 130 currently known or later developed may be modified and adopted for use herein. The image sensors 130, in some implementations, include color filter arrays (CFAs). Referring now to FIG. 2, the image sensors 130 may include Bayer CFAs (sometimes referred to as a Bayer filter). Bayer CFAs include a mosaic CFA for arranging red, green, and blue color filters on a grid of photosensors. As illustrated in FIG. 2, the filter pattern is 50% green, 25% red, and 25% blue, as human eyes are most sensitive to green light. Thus, each pixel is filtered to record only one of the three colors, and various well-known de-mosaicking algorithms are used to obtain full-color images. In some examples, the WL image sensor 130a and the FL image sensor 130b are different sensors with the same or different resolutions. In other examples, the sensors 130 are identical sensors. Identical sensors (e.g., the same resolution, geometry, etc.) often improves and eases manufacturing, assembly, and alignment of the system 100.

Figure 3:
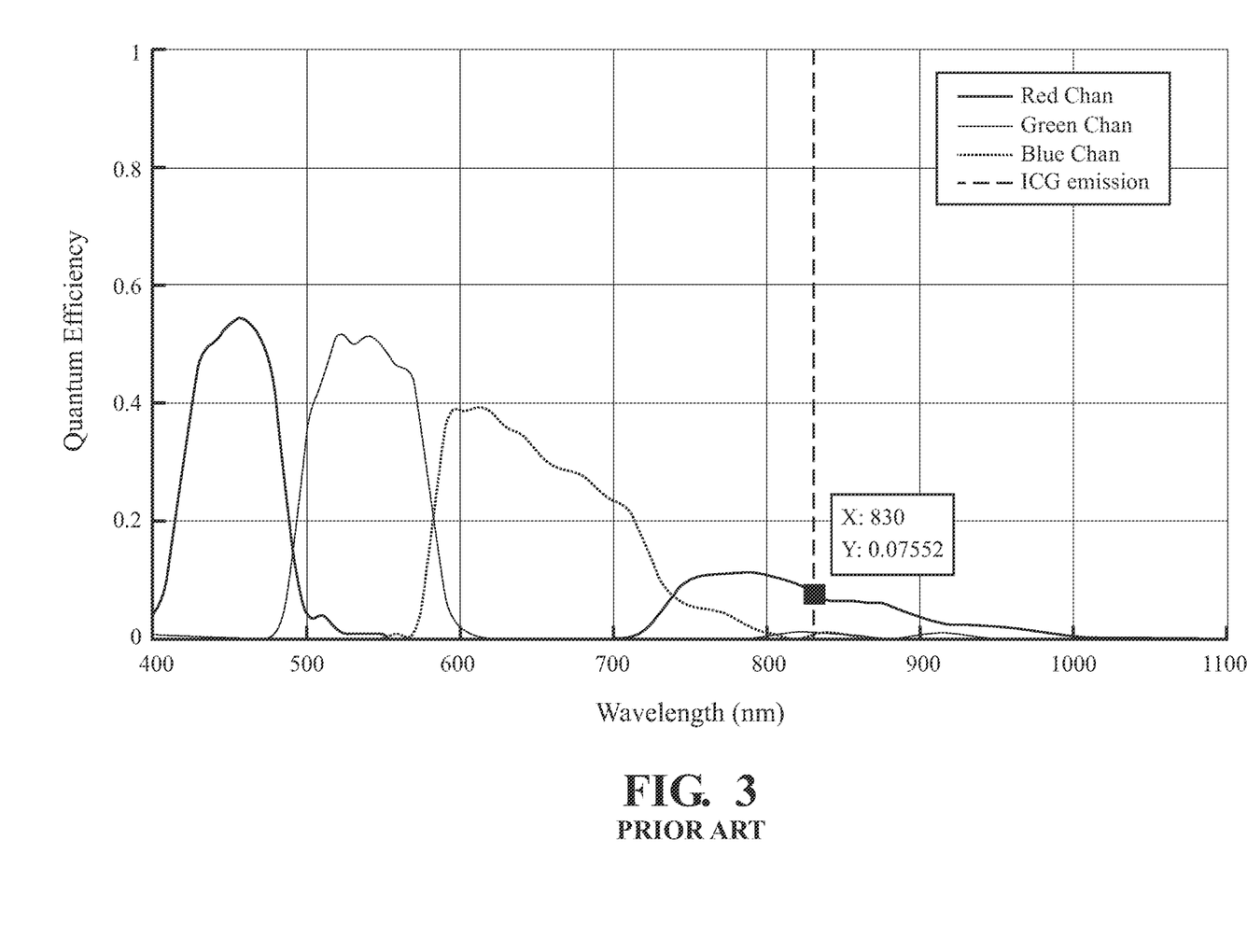
FIG. 3 is a graph of quantum efficiency versus wavelength for known image sensors.
Figure 4:
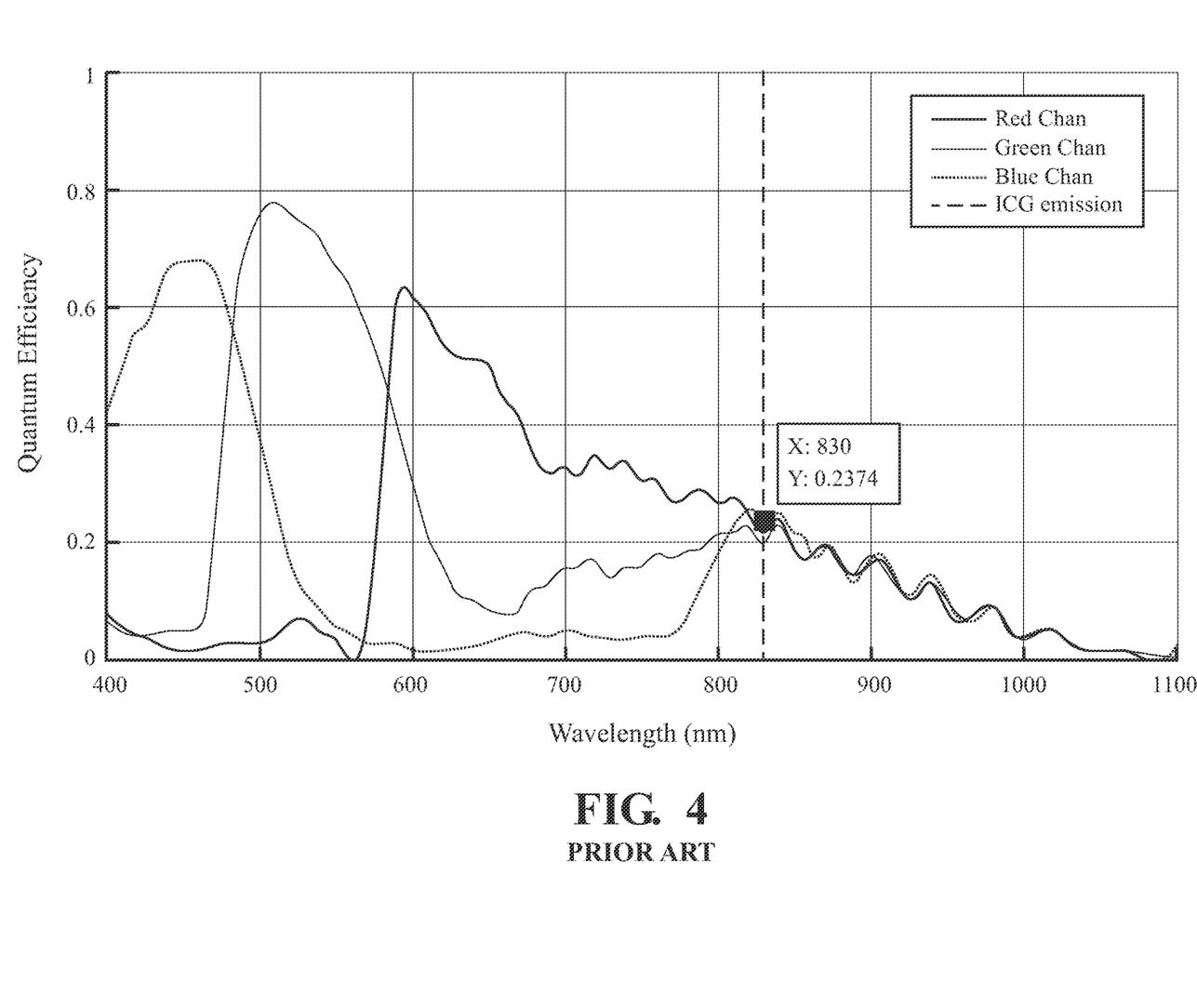
FIG. 4 is a graph of quantum efficiency versus wavelength for the image sensor of FIG. 2.

The dual image sensors 130 may exhibit greatly increased quantum efficiency relative to a, for example, three (3) CCD RGB prism assembly. FIG. 3 illustrates the quantum efficiency of the three (3) CCD RGB prism assembly, which exhibits a quantum efficiency of only 8% with blue channel out-of-band transmission at the ICG fluorescence center wavelength of 830 nm. That is, the illustrated assembly only captures approximately 8% of the photons that the sensor receives from the ICG fluorescence. In contrast, FIG. 4 illustrates the quantum efficiency of nearly 24% of the prism 120 and image sensors 130 of the present disclosure. In addition, FIG. 4 illustrates a near neutral response of the sensors' output at the ICG fluorescence center wavelength of 830 nm.

With reference again to FIG. 1, the sensors 130 transmit WL data 132a and FL data 132b to a camera control unit (CCU) 140. The CCU 140 may, in some examples, be included within the camera head unit 102, while in other examples is remote from the camera head unit 102. The CCU 140 includes computing resources 142 (e.g., data processing hardware) and storage resources 144 (e.g., memory hardware). In some implementations, the CCU 140 is disposed physically at the system 100 (e.g., within the camera head unit 102) and in wired communication with the sensors 130. In other implementations, the CCU 140 is in wireless communication with the sensors 130 (e.g., via wireless, Bluetooth, etc.) and may be remote from the sensors 130 and/or system 100. In this case, the CCU 140 may correspond to any appropriate computing device 900 (see FIG. 9), such as a desktop workstation, laptop workstation, or mobile device (e.g., smart phone or tablet). In yet other implementations, the data 132 may be stored in nonvolatile storage at the system 100 (e.g., a thumb drive) and later removed to be processed at data processing and memory hardware 140, 142 remote from the sensors 130.

The data processing hardware 142 executes (i.e., using instructions stored on the storage resources 144) a fluorescence image enhancer 150. In some implementations, the fluorescence image enhancer 150 executes one of a plurality of finite impulse response (FIR) filter. A FIR filter has an impulse response of finite duration (i.e., the output will eventually settle to zero). FIR filters require no feedback and are inherently stable and easily provide a linear phase response, making them ideal for phase-sensitive applications such as image processing. One of the FIR filters may be a diffusion contrast-loss equalization filter 200. In some examples, the diffusion contrast-loss equalization filter 200 is a digital FIR filter. The diffusion contrast-loss equalization filter 200 compensates for contrast loss due to, for example, ICG diffusion. As ICG naturally diffuses, the contrast (i.e., the difference in color that allows objects to be distinguishable) decreases, which in turn decreases the effectiveness of the diagnostic nature of the image.

Figure 5A:
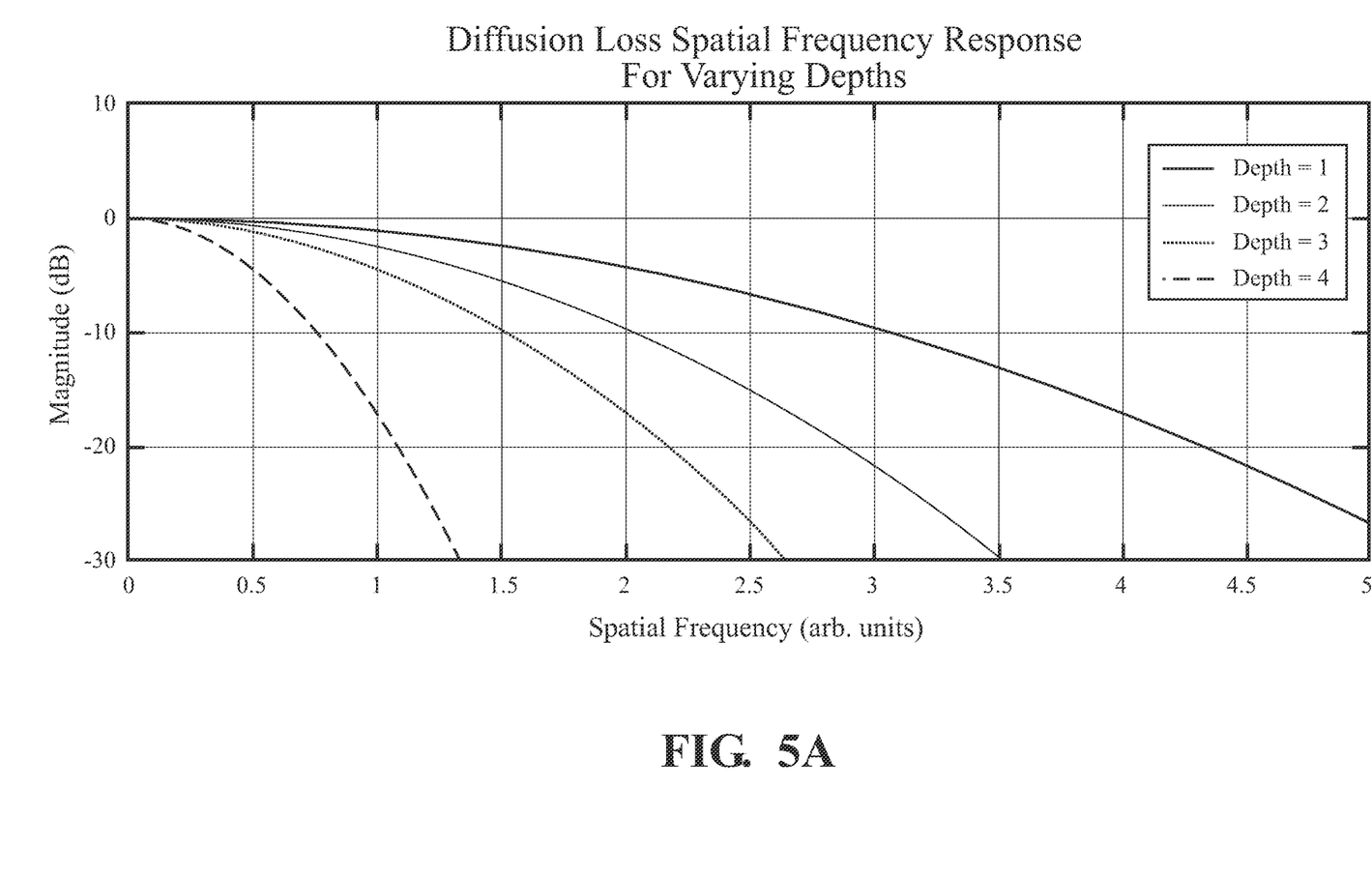
FIG. 5A is a graph of exemplary diffusion loss spatial frequency response for varying depths of tissue.
Figure 5B:
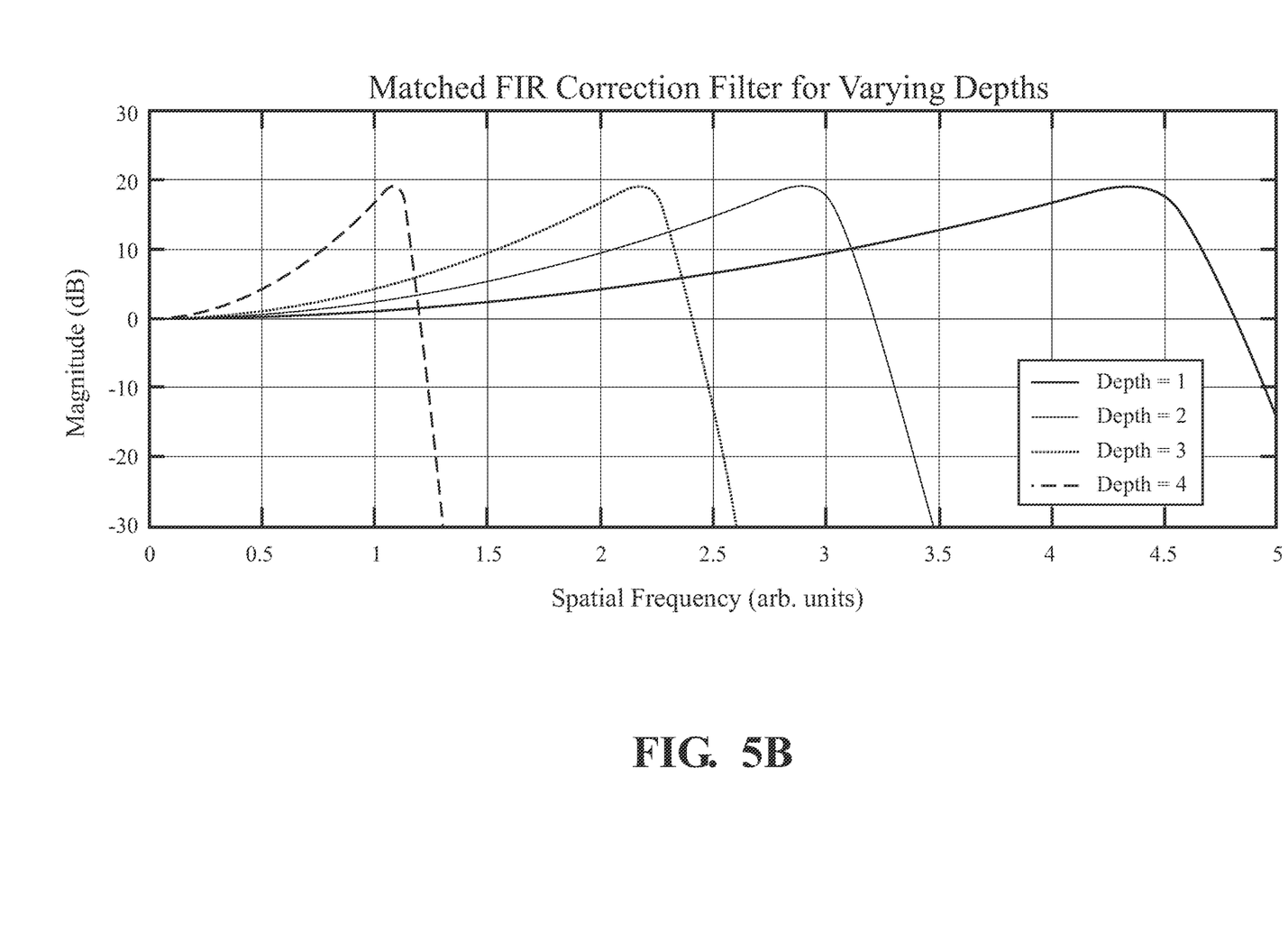
FIG. 5B is a graph of exemplary matched finite impulse response correction filters for the varying depths of tissue of FIG. 5A.
Figure 5C:
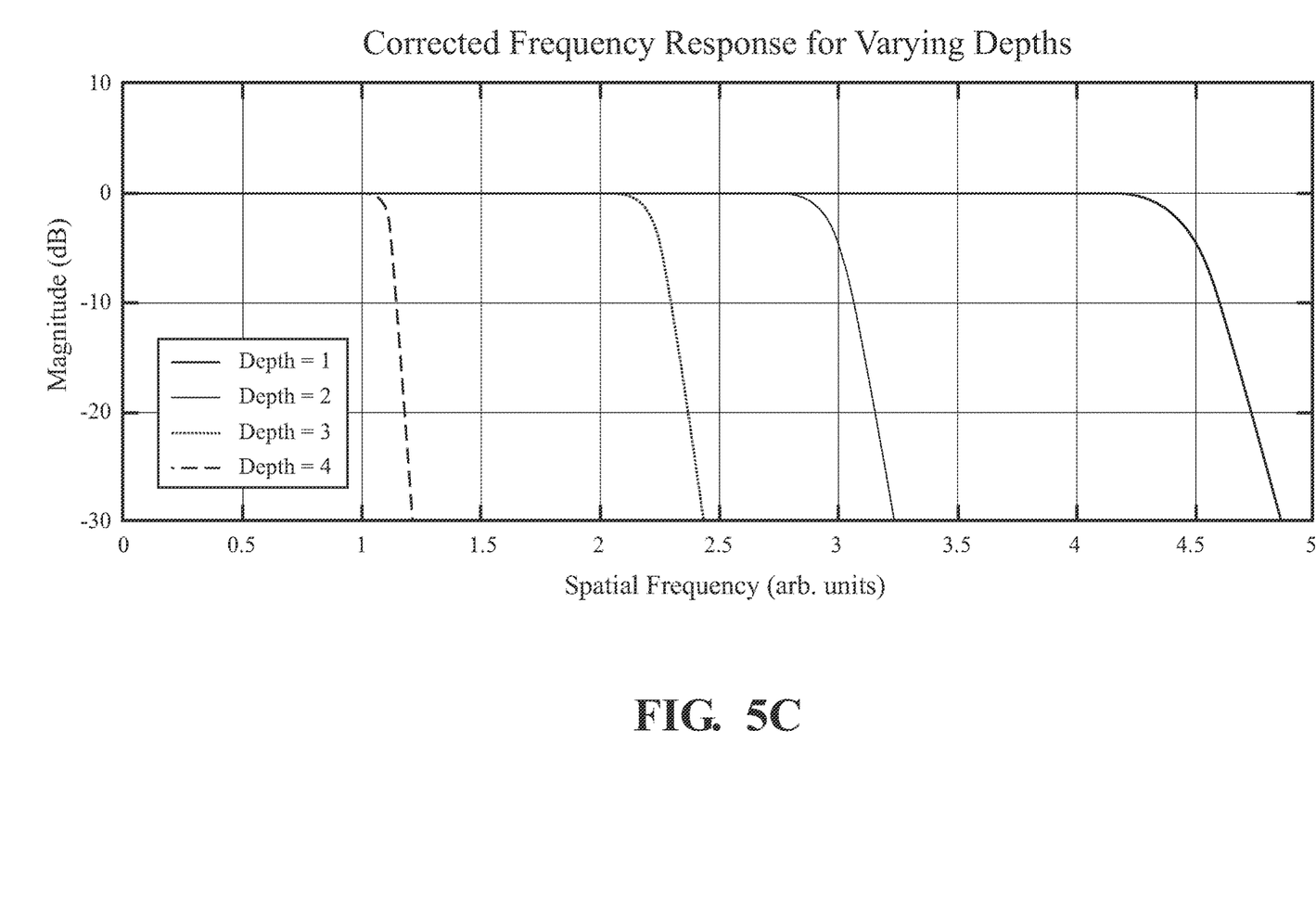
FIG. 5C is a graph of corrected frequency responses for the varying depths of tissue of FIGS. 5A and 5B.

In addition to this natural diffusion, the depth of view into the tissue also diffuses the dye. That is, the deeper into the tissue that is imaged, the more diffused the ICG. For example, for every millimeter of tissue depth, image contrast may be reduced. This diffusion (i.e., loss of contrast) may be represented as a Gaussian blur. For example, the surface of the tissue may be represented as a point spread function, and as the viewpoint moves deeper into the tissue, the Gaussian blur increases. Referring now to FIG. 5A, diffusion loss spatial frequency response is illustrated for four exemplary and arbitrary tissue depths. As the depth increases, the maximum spatial frequency decreases. This Gaussian blur (i.e., the ICG diffusion) has a Gaussian impulse response and Gaussian frequency response that may be matched by the diffusion contrast-loss equalization filter 200. That is, the filter 200 may invert the Gaussian blur (e.g., the frequency response) to increase the contrast of the ICG. Referring now to FIG. 5B, the frequency response for four matched FIR correction filters for the arbitrary depths provided in FIG. 5A are illustrated. In some examples, the correction filter(s) 200 are gain limited to approximately 10 to 30 dB (e.g., 20 dB). FIG. 5C illustrates the cascade of the contrast loss spatial frequency response and the FIR correction filter for each exemplary depth. In some implementations, the system 100 includes a single filter 200 with adaptive parameters. In other implementations, the system includes a plurality of filters 200 with different parameters (e.g., frequency responses) that may be automatically selected by the system 100 (e.g., based on input measurements such as ambient light levels or based on image analysis) or manually selected by a user. For example, the user may access a menu and select from among the different filters 200 depending on the amount of natural diffusion (i.e., based on a temporal nature) or the depth of the imaging within the tissue. Each filter 200 may select for a desired intensity of contrast.

As stated above, the fluorescence image enhancer 150 executes one or more FIR filters. For example, the fluorescence image enhancer 150 may also execute a WL-FL co-site alignment digital FIR filter 300. The image sensors 130 are typically fixed in place and the prism 120 directs light toward each sensor 130. The placement of the sensors 130 must be very precise to keep the white light and IR light spatially aligned (i.e., the sensors must be placed exactly where the prism directs the light). Such precise alignment is difficult to obtain and, after separation through the prism 120 (e.g., because of minor misalignment or misplacement of the image sensors 130), the WL data 132a and the FL data 132b may be out of alignment. This misalignment or misregistration leads to artifacts and defects after combining the data 132 to create the combined image data 170. To correct this misalignment, the phase alignment filter 300 includes a customized linear phase response that spatially aligns the WL data 132a and the FL data 132b. That is, in some examples, the alignment filter 300 shifts the FL data 132b (or, alternatively, the WL data 132a) in space (in one or two dimensions) by linearly shifting the phase response. Failure to compensate for the misalignment between the image sensors 130 will decrease the sharpness (i.e., increase blurriness) in the combined image data 170.

In some examples, the misalignment of the sensors 130 may be measured during manufacturing and the alignment filter 300 may be calibrated after determining the misalignment. Optionally, the system 100 may include a plurality of alignment filters 300 (i.e., a plurality of precomputed filters 300 stored in memory 144) with different parameters (e.g., different linear phase responses) and the system 100 or the user may select which filter best compensates for the misalignment of the sensors 130. For example, each successive alignment filter 300 may adjust an image by one half of a pixel horizontally or vertically, or in combination.

In some examples, the fluorescence image enhancer 150 executes an adaptive low light sensitivity digital FIR filter 400 to adaptively control the sensitivity improvement of the enhancer 150 based on received light levels. That is, the adaptive light sensitivity filter 400 allows the enhancer 150 to tradeoff between sensitivity and contrast by adjusting the sensitivity and the contrast of the FL data 132*b* depending on lighting conditions. For example, when the received light level is below a threshold level, the adaptive light sensitivity filter 400 may decrease the contrast and increase the sensitivity. In some examples, the threshold may be 10 microwatts per square centimeter per steradian. Similarly, when the ambient light level is above the threshold level (or a second, different threshold level), the adaptive light sensitivity filter 400 may increase the contrast and decrease the sensitivity. Because of the nature of medical diagnostic dyes such as ICG (i.e., the diffuse nature after binding with the test subject), it is often advantageous to sacrifice sharpness and/or contrast in favor of sensitivity because the contrast is often of limited value. In some examples, the system 100 (e.g., at sensor 130*b*) measures or determines an amount of fluorescent light received, and the adaptive light sensitivity filter 400 decreases contrast and increases sensitivity when the measured or determined amount of light is below a threshold amount of watts per square centimeter per steradian. Similarly, the adaptive light sensitivity filter 400 may increase the contrast and decrease the sensitivity when the amount of light is above the same or different threshold amount of watts per square centimeter per steradian.

For example, to increase sensitivity at the expense of contrast (i.e., filter bandwidth), the adaptive light sensitivity filter 400 may increase an amount of accumulation (i.e., increase the sum of one or more pixels values) over a neighborhood (i.e., a select pixel and a group or sub-set of pixels that surround the select pixel) of the FL data 132*b*. That is, instead of performing any binning in or at the image sensor 130*b* itself, the filter 400 allows the system 100 to adaptively adjust the amount of light accumulation in a neighborhood based on the measured light levels. Binning (as discussed in more detail below) refers to the process conducted by some CCD image sensors where light from multiple pixels is added together, thereby decreasing resolution but increasing sensitivity. The system may include (i.e., in memory storage 144), a plurality of filters 400 with different amount of accumulations that the system 100 or the user may select from based on FL light levels. For example, the system 100 may include a filter 400 that accumulates light at an amount similar to 2×2 binning, 4×4 binning, 8×8 binning, 16×16 binning, etc. When the amount of FL light is sufficiently high, the system 100 may not apply the adaptive light sensitivity filter 400 at all. The adaptive light sensitivity filter 400 may adjust the amount of light accumulated with a low pass filter that has a cutoff at a threshold frequency and a magnitude of a frequency response. The tradeoff between the cutoff frequency and the magnitude adjusts the tradeoff between sensitivity and contrast.

Figure 6:
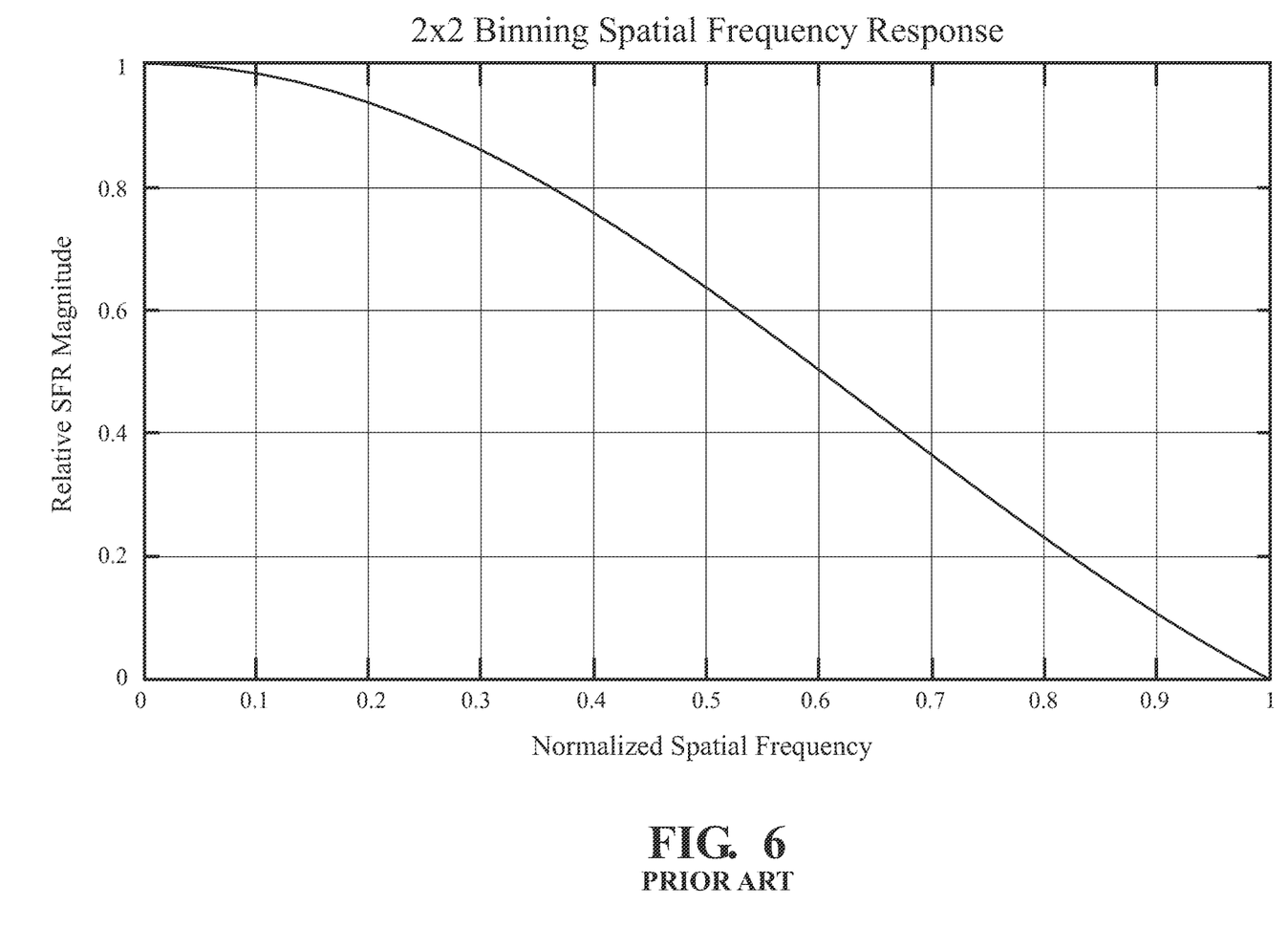
FIG. 6 is a plot of a spatial frequency response of a 2×2 binning process.

Optionally, the fluorescence image enhancer 150 includes a Nyquist suppression filter 500. Typically, endoscopes, when processing captured image data, will conduct a 2×2 binning process. As briefly described above, binning is the common process of combining the values from adjacent pixels (horizontal and/or vertical) to increase readout speed and improve signal to noise ratio and sensitivity at the expense of resolution. When conducting a 2×2 binning process, the values captured by four adjacent pixels are combined together. Typical endoscopes will conduct 2×2 binning, then downsample from ultra high definition (UHD) to high definition (HD). The endoscope will then perform any desired processing on the HD image data prior to upsampling back to UHD. This results in contrast-loss SFR errors (from the binning) and aliasing (from the downsampling and upsampling). Referring now to FIG. 6, this common approach leads to suboptimal spatial frequency response, as there is significant magnitude loss as the frequency approaches the Nyquist frequency (i.e., the bottom-right corner of the plot of FIG. 6).

In contrast, the Nyquist suppression filter 500 of the fluorescence image enhancer 150 provides improvement over the 2×2 (i.e., 2 horizontal by 2 vertical) binning SFR process used by typical endoscopes by instead using larger-extent digital FIR filtering with a maximally flat magnitude response and magnitude response zeros at horizontal and vertical Nyquist (relative to the sampling spectrum of the FL image sensor 130*b*) to remove color filter array modulation. The color filter array modulation may be removed because the system 100 treats the FL image sensor 130*b* like a monochrome sensor.

Figure 7:
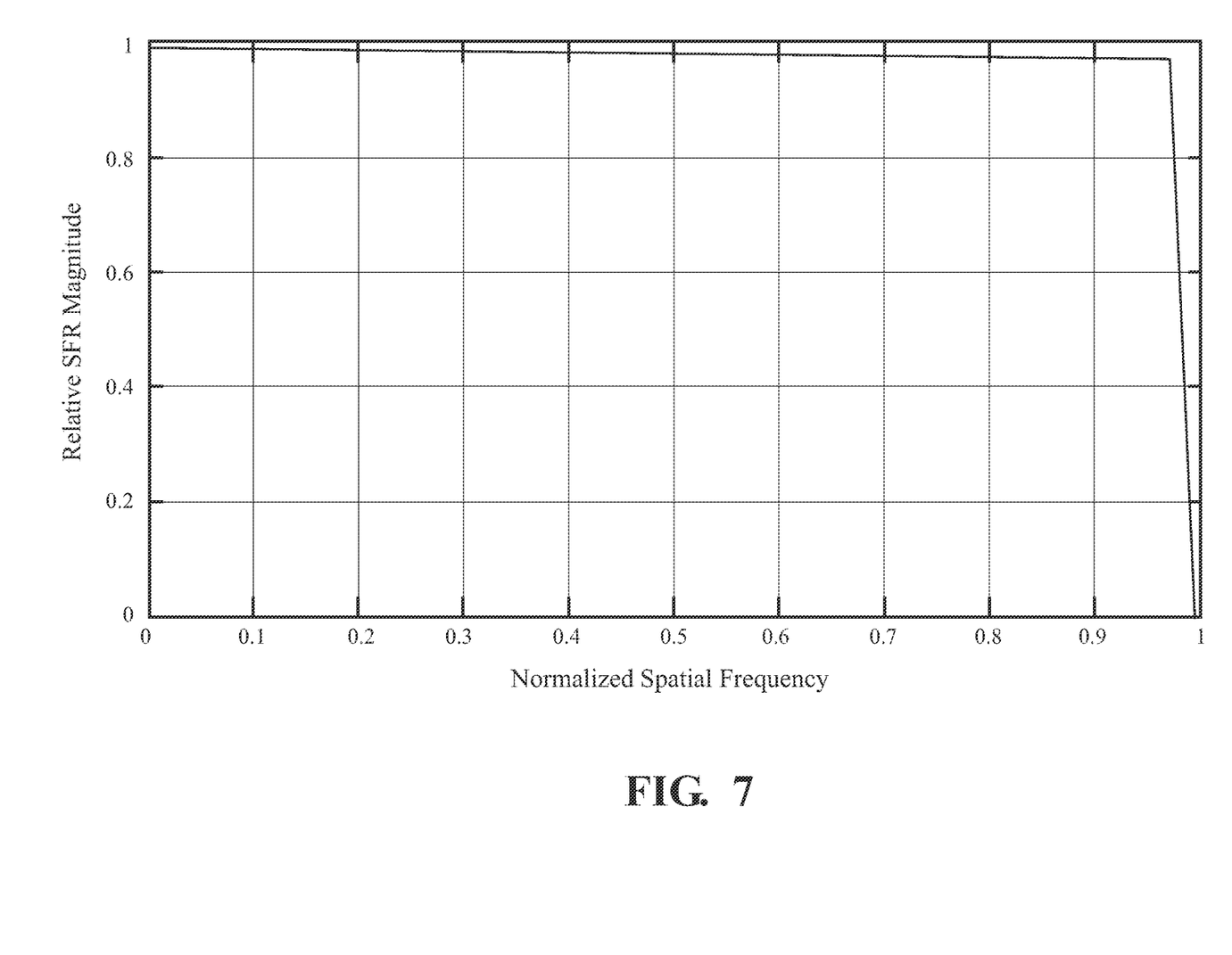
FIG. 7 is a plot of a spatial frequency response of an adaptive virtual binning process in accordance with the present disclosure.

Referring now to FIG. 7, the SFR of the Nyquist suppression filter 500 achieves a magnitude of zero at the horizontal and the vertical Nyquist frequency (i.e., the bottom-right corner of the plot of FIG. 7) while maintaining a maximum or near maximum frequency response at the remaining frequencies. The filter 500 provides an extended precision low-pass magnitude response used as an "adaptive virtual binning process." That is, the filter 500, instead of a fixed 2×2 binning process, provides a much finer "virtual binning process". That is, instead of actual binning on the image sensors 130, the filter 500 allows for smooth and dynamic control over the frequency response of the image data 132.

The fluorescence image enhancer 150, after processing and enhancing the FL data 132*b*, outputs the enhanced FL data 160. The enhanced FL data 160 may be combined or superimposed with the WL data 132*a* to create the combined image data 170. In other examples, the light source 110 switches between emitting WL light 112*a* and NIR light 114*a*, and thus the combined image data switches between consisting of WL data 132*a* and enhanced FL data 160 (e.g., each frame alternates between WL data 132*a* and FL data 160). Thus, the combined image data 170 includes the enhanced FL data 160 and/or the WL data 132*a* (which may or may not be further processed). The combined image data 170 is transmitted to the display 180, which processes the image 170 to generate a visible image (i.e., a picture or video).

Accordingly, the endoscopic system 100 provided may reconstruct a baseband image (e.g., an ICG baseband image) from CFA channels with minimal CFA modulation and maximally flat spatial frequency response (SFR) while improving the sensitivity of the ICG sensor output. Further, the system 100 may adaptively control sensitivity improvement by using an extended precision parametrically controlled 2D low-pass filter, correct for misregistration of the ICG and WL prism output images, and correct for diffusion-based contrast loss in the ICG image. While four separate filters 200, 300, 400, 500 are illustrated and described, it should be appreciated that the four filters 200, 300, 400, 500 may be combined in any combination to result in one to four filters without departing from the spirit and scope of the disclosure.

Figure 8:
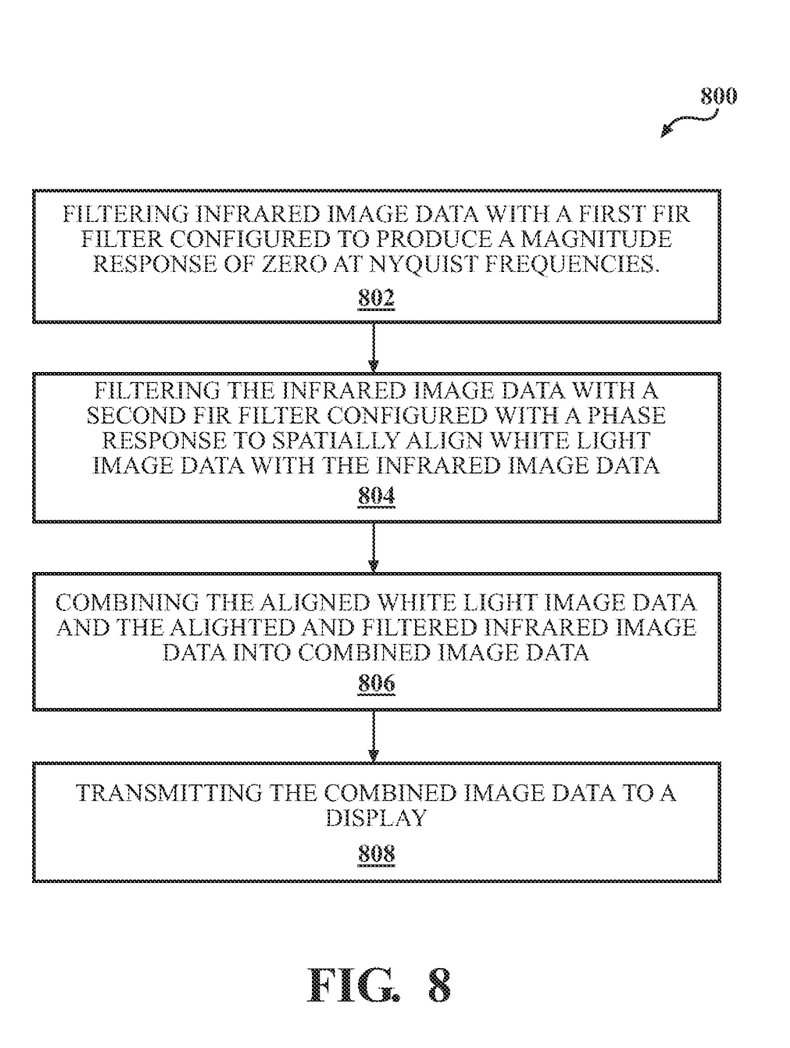
FIG. 8 is a flowchart of an example method enhancing fluorescence imaging.

FIG. 8 is a flowchart of example operations 800 for a fluorescence imaging system 100 that is configured to generate a video image onto a display 180. The system 100 includes a light source 110 for emitting infrared light 114*a* and white light 112a, an infrared (or fluorescent) image sensor 130b for capturing infrared image data 132b in the infrared spectrum, and a visible light image sensor 130a for capturing visible light image data 132a in the visible light spectrum. The system 100 also includes data processing hardware 142 in communication the infrared image sensor 130b and the white light image sensor 130a. Memory hardware 144 in communication with data processing hardware 142 stores instructions that when executed on the data processing hardware 142 cause the data processing hardware 142 to perform operations. The operations include, at step 802, filtering the infrared image data 132b with a first digital finite impulse response (FIR) filter 500 configured to produce a magnitude response of zero at a horizontal Nyquist frequency and a vertical Nyquist frequency.

At step 804, the operations include filtering the infrared image data 132b with a second digital FIR filter 300 configured with a phase response to spatially align the white light image data 132a with the infrared image data 132b. At step 806, the operations include combining the aligned white light image data 132a and the aligned and filtered infrared image data 132b into combined image data 170, and at step 808, transmitting the combined image data 170 to the display 180. That is, in some examples, both white light image data 132a and infrared image data 132b is transmitted to the display 180 (e.g., each frame alternates between WL data and FL data) and the display 180 displays some combination of the WL data 132a and the FL data 132b for the user.

Figure 9:
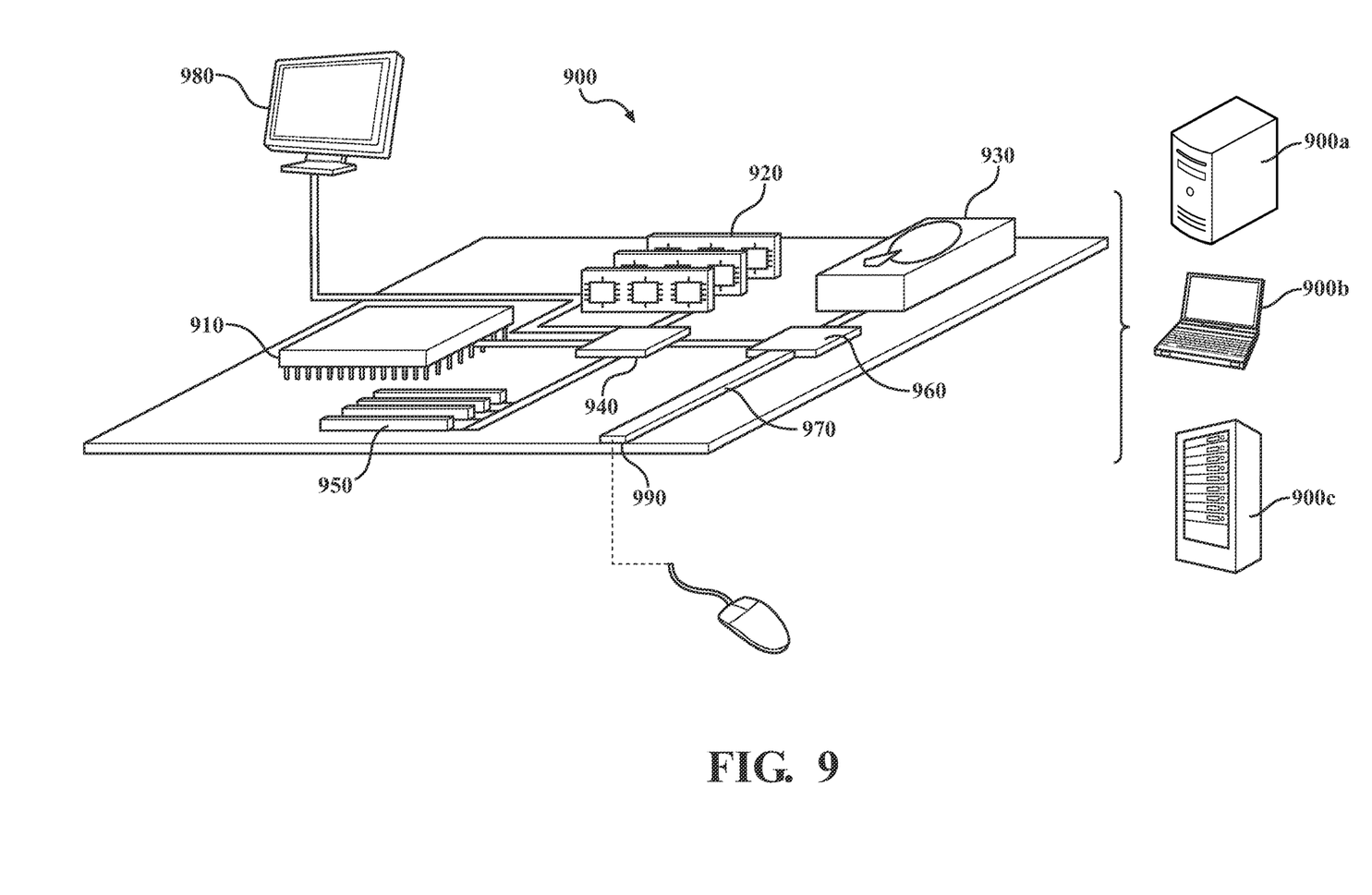
FIG. 9 is a schematic view of an example computing device that may be used to implement the systems and methods described herein.

FIG. 9 is schematic view of an example computing device 900 (e.g., data processing hardware 142 and memory hardware 144) that may be used to implement the systems and methods described in this document. For examples, computing device 900 may perform tasks such as controlling the light source 110 (e.g., enabling and disabling the light source, switching between white light and MR light, etc.), configuring and communicating with the image sensors 130 (e.g., receiving the image data), and implementing and executing one or more of the digital FIR filters 200, 300, 400, 500. In some examples, the computing device 900 transmits image data to the display 180. That is, using the data received from the image sensors 130, the computing device 900 may store and execute instructions or operations to implement any number of the digital FIR filters 200, 300, 400, 500. The computing device 900 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the disclosures described and/or claimed in this document.

The computing device 900 (e.g., data processing hardware 142) includes a processor 910, memory 920, a storage device 930, a high-speed interface/controller 940 connecting to the memory 920 and high-speed expansion ports 950, and a low speed interface/controller 960 connecting to a low speed bus 970 and a storage device 930. Each of the components 910, 920, 930, 940, 950, and 960, are interconnected using various busses, and may be mounted on a common motherboard or in other manners as appropriate. The processor 910 can process instructions for execution within the computing device 900, including instructions stored in the memory 920 or on the storage device 930 to display graphical information for a graphical user interface (GUI) on an external input/output device, such as display 980 coupled to high speed interface 940. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 920 stores information non-transitorily within the computing device 900. The memory 920 may be a computer-readable medium, a volatile memory unit(s), or non-volatile memory unit(s). The non-transitory memory 920 may be physical devices used to store programs (e.g., sequences of instructions) or data (e.g., program state information) on a temporary or permanent basis for use by the computing device 900. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 830 is capable of providing mass storage for the computing device 800. In some implementations, the storage device 830 is a computer-readable medium. In various different implementations, the storage device 830 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 820, the storage device 830, or memory on processor 810.

The high speed controller 840 manages bandwidth-intensive operations for the computing device 800, while the low speed controller 860 manages lower bandwidth-intensive operations. Such allocation of duties is exemplary only. In some implementations, the high-speed controller 840 is coupled to the memory 820, the display 880 (e.g., through a graphics processor or accelerator), and to the high-speed expansion ports 850, which may accept various expansion cards (not shown). In some implementations, the low-speed controller 860 is coupled to the storage device 830 and a low-speed expansion port 890. The low-speed expansion port 890, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 800a or multiple times in a group of such servers 800a, as a laptop computer 800b, or as part of a rack server system 800c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A fluorescence imaging system for use in a medical procedure, the imaging system configured to generate a video image onto a display, the fluorescence imaging system comprising:
    a light source for emitting infrared light and white light;
    an infrared image sensor for capturing infrared image data in the infrared spectrum;
    a white light image sensor for capturing white light image data in the white light spectrum;
    data processing hardware in communication with the infrared image sensor and the white light image sensor; and
    memory hardware in communication with the data processing hardware, the memory hardware storing instructions that when executed on the data processing hardware cause the data processing hardware to perform operations comprising:
        filtering the infrared image data with a fluorescence image enhancer having both a first digital finite impulse response (FIR) filter and a second digital FIR filter different from the first FIR filter, wherein the first digital FIR filter is configured to produce a magnitude response of zero is at a horizontal Nyquist frequency and a vertical Nyquist frequency and the second digital FIR filter is configured with a phase response to spatially align the white light image data with the infrared image data;
        combining the white light image data and the filtered infrared image data into combined image data; and
        transmitting the combined image data to the display.

2. The fluorescence imaging system of claim 1, wherein the first digital FIR filter is configured to equalize for contrast loss from fluorescence diffusion and the second digital FIR filter is configured with a phase response to spatially align the white light image data with the infrared image data.

3. The fluorescence imaging system of claim 2, wherein the third digital FIR filter is further configured to be gain limited to 20 dB.

4. The fluorescence imaging system of claim 1, wherein the first digital FIR filter is configured to equalize for contrast loss from fluorescence diffusion and the second digital FIR filter is configured to adjust a sensitivity of the infrared image data and a contrast of the infrared image data based on received infrared light.

5. The fluorescence imaging system of claim 4, wherein the second digital FIR filter is configured to adjust the sensitivity and the contrast of the infrared image data by adjusting an accumulation of light in a neighborhood of the infrared image data.

6. The fluorescence imaging system of claim 4, wherein the second digital FIR filter comprises a low pass filter with a cutoff frequency and a magnitude of a frequency response.

7. The fluorescence imaging system of claim 6, wherein the second digital FIR filter is further configured to increase the sensitivity of the infrared image data and decrease the contrast of the infrared image data when the received infrared light is below a threshold level.

8. The fluorescence imaging system of claim 7, wherein the threshold level is 10 microwatts.

9. The fluorescence imaging system of claim 7, wherein the second digital FIR filter is further configured to increase the sensitivity of the infrared image data by increasing the magnitude and decrease the contrast of the infrared image data by decreasing the cutoff frequency when the received infrared light is below a threshold level.

10. The fluorescence imaging system of claim 7, wherein the second digital FIR filter is further configured to decrease the sensitivity of the infrared image data and increase the contrast of the infrared image data when the received infrared light is above a threshold level.

11. The fluorescence imaging system of claim 7, wherein the third digital FIR filter is further configured to decrease the sensitivity of the infrared image data by decreasing the magnitude and increase the contrast of the infrared image data by increasing the cutoff frequency when the received infrared light is below a threshold level.

12. The fluorescence imaging system of claim 1, wherein the infrared image sensor and the white light image sensor have the same resolution.

13. The fluorescence imaging system of claim 1, wherein the infrared image sensor comprises a near infrared image sensor.

14. The fluorescence imaging system of claim 1, wherein the infrared image sensor and the white light image sensor comprise a Bayer color filter array.

15. The fluorescence imaging system of claim 1, further comprising a dichroic prism, wherein the dichroic prism splits received light into white light and infrared light, and wherein the infrared image sensor receives the infrared light from the dichroic prism, and wherein the white light image sensor receives the white light from the dichroic prism.

16. The fluorescence imaging system of claim 1, wherein the first digital FIR filter is further configured to produce a flat magnitude response prior to the horizontal Nyquist frequency and the vertical Nyquist frequency.

17. The fluorescence imaging system of claim 1, wherein the second digital FIR filter is configured to spatially adjust a position of the infrared image data in two dimensions.

18. The fluorescence imaging system of claim 1, wherein the second digital FIR filter is configured to adjust an image by at least one of one half of a pixel horizontally or one half of a pixel vertically.

\* \* \* \* \*